United States Patent [19]

Allen et al.

[11] Patent Number: 5,202,322
[45] Date of Patent: Apr. 13, 1993

[54] QUINAZOLINONE AND PYRIDOPYRIMIDINE A-II ANTAGONISTS

[75] Inventors: Eric E. Allen, Edison, N.J.; Richard E. Olson, Wilmington, Del.

[73] Assignees: Merck & Co., Inc., Rahway, N.J.; E. I. du Pont de Nemours and Company, Wilmington, Del.

[21] Appl. No.: 765,626

[22] Filed: Sep. 25, 1991

[51] Int. Cl.$^5$ .................. A61K 31/54; A61K 31/505; C07D 239/90; C07D 239/96
[52] U.S. Cl. ..................... 514/228.2; 514/234.2; 514/234.5; 514/228.5; 514/255; 514/259; 514/260; 544/284; 544/285; 544/287; 544/116; 544/117; 544/57; 544/58.6
[58] Field of Search .............. 544/284, 285, 58.6, 544/57, 116, 287; 514/255, 259, 260, 234.5, 228.2

[56] References Cited

FOREIGN PATENT DOCUMENTS 407342 1/1991 European Pat. Off. .
411766 2/1991 European Pat. Off. .

Primary Examiner—Mukund J. Shah
Assistant Examiner—Matthew V. Grumbling
Attorney, Agent, or Firm—William H. Nicholson; Joseph F. DiPrima

[57] ABSTRACT

Substituted quinazolinones and pyridopyrimidines of structural formula 1

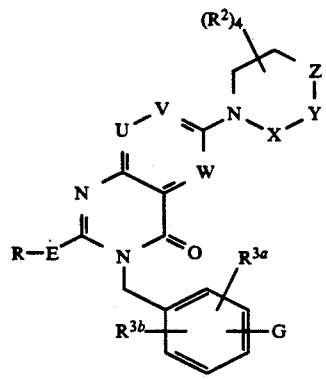

are angiotensin II antagonists useful in the treatment of disorders related to the reninangiotensin system (RAS) such as hypertension, congestive heart failure, ocular hypertension and certain CNS disorders.

12 Claims, No Drawings

QUINAZOLINONE AND PYRIDOPYRIMIDINE A-II ANTAGONISTS

SUMMARY OF THE INVENTION

This invention is concerned with novel quinazolinones and pyridopyrimidines of structural formula I

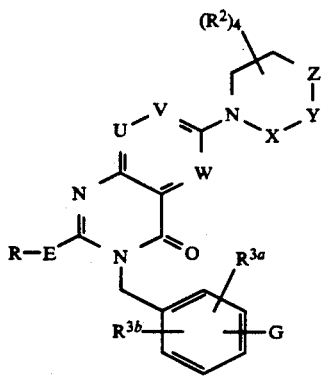

wherein X, Y and Z are carbons or a hetero-atoms such as nitrogen, oxygen or sulfur and G is $R^1$ or

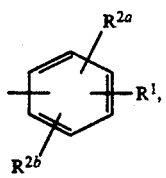

R is usually alkyl and $R^1$ is an acidic function. The compounds are angiotensin II antagonists useful in the treatment of disorders related to the reninangiotensin system such as hypertension, and congestive heart failure.

This invention also relates to the use of the novel compounds and ophthalmic formulations thereof in the topical treatment of ocular hypertension and glaucoma associated therewith.

This invention is also concerned with the use of the novel compounds in the treatment of certain CNS disorders such as cognitive dysfunction.

The invention is also concerned with novel pharmaceutical and ophthalmic formulations comprising one of the novel compounds as active ingredient either alone or in combination with other active ingredients.

Finally, the invention is concerned with novel processes for the preparation of the novel compounds.

BACKGROUND OF THE INVENTION

The renin-angiotensin system (RAS) plays a central role in the regulation of normal blood pressure and seems to be critically involved in hypertension development and maintenance as well as congestive heart failure. Angiotension II (AII), an octapeptide hormone is produced mainly in the blood during the cleavage of angiotension I by angiotension converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption (M. Antonaccio. Clin. Exp. Hypertens. A4, 27–46 (1982); D. H. P. Streeten and G. H. Anderson, Jr. -Handbook of Hypertension, Clinical Pharmacology of Antihypertensive Drugs, ed. A. E. Doyle, Vol. 5, pp. 246–271, Elsevier Science Publisher, Amsterdam, The Netherlands, 1984).

Recently, several non-peptide compounds have been described as AII antagonists. Illustrative of such compounds are those disclosed in U.S. Pat. Nos. 4,207,324; 4,340,598; 4,576,958; 4,582,847 and 4,880,804 in European Patent Applications 028,834; 245,637; 253,310; and 291,969; and in articles by A. T. Chiu, et al. (Eur. J. Pharm. Exp. Therap, 157, 13–21 (1988)) and by P. C. Wong, et al. (J. Pharm. Exp. Therap, 247, 1–7(1988), Hypertension, 13, 489–497 (1989)). All of the U.S. patents, European Patent Applications 028,834, 253,310, 399,731 and 400,974 and the two articles disclose substituted imidazole compounds which are generally bonded through a lower alkyl bridge to a substituted phenyl.

Also, U.S. patent applications, Ser. Nos. 07/537,891 (filed Jun. 18, 1990) and 07/665,389 (filed Mar. 6, 1991) disclose quinazolinones with substitution patterns different from those disclosed herein which are also Angiotensin II antagonists.

DETAILED DESCRIPTION

The novel compounds of the invention are represented by structural formula 1

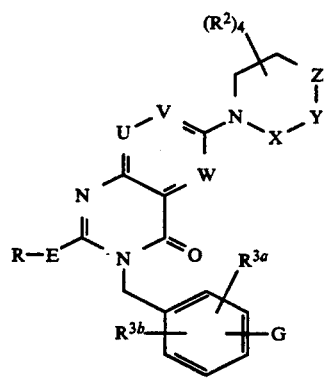

or a pharmaceutically acceptable salt thereof, wherein.
G is
  (1) $R^1$ or

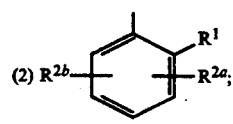

E is
  (1) a single bond,
  (2) —CH(OH)—,
  (3) —O—,
  (4) —CO—,
  (5) —S(O)$_x$(CH$_2$)$_s$— wherein x is 0, 1, or 2, and s is 0–5, or (6) —NR³(CH₂)ₛ— wherein R³ is
  (a) —H,
  (b) C₂₋₄ alkanoyl,
  (c) C₁₋₆ alkyl,
  (d) C₂₋₆ alkenyl,
  (e) C₃₋₇ cycloalkyl,
  (f) phenyl, or
  (g) benzyl;
R is
(1) aryl,
(2) heteroaryl,
(3) C₃₋₇ cycloalkyl,
(4) polyfluoro-C₁₋₄ alkyl,
(5) —H,
(6) C₂₋₆ alkenyl,
(7) C₂₋₆ alkynyl,
(8) C₁₋₆ alkyl, either unsubstituted or substituted with:
  (a) aryl,
  (b) C₃₋₇ cycloalkyl,
  (c) halo,
  (d) —NH₂,
  (e) —NH(C₁₋₄ alkyl),
  (f) —N(C₁₋₄ alkyl)₂,
  (g) —OR⁴, wherein R⁴ is
    (i) —H,
    (ii) aryl,
    (iii) heteroaryl,
    (iv) C₁₋₆ alkyl, or
    (v) aryl-C₁₋₆ alkyl;
  (h) —COOR⁴,
  (i) —NHSO₂R⁴, or
  (j) —SO₂NHR⁵, wherein R⁵ is
    (i) —H
    (ii) C₁₋₅ alkyl,
    (iii) aryl or,
    (iv) —CH₂-aryl;
R¹ is
(1) —CO₂R⁴
(2) —SO₃R⁶, wherein R⁶ is
  (a) —H
  (b) —CH(R⁴)—O—CO—R⁴ᵃ wherein R⁴ᵃ is
    (i) C₁₋₆ alkyl,
    (ii) aryl or
    (iii) —CH₂-aryl;
(3) —P(O)(OR⁶)₂,
(4) —CONHNHSO₂CF₃,
(5) —SO₂NHCN,
(6) —P(O)(OR⁶)(OR⁴),
(7) —SO₂NHR⁷, wherein R⁷ is
  (a) —H
  (b) aryl,
  (c) heteroaryl,
  (d) C₃₋₇ cycloalkyl,
  (e) polyfluoro-C₁₋₄ alkyl, or
  (f) C₁₋₁₀ alkyl, either unsubstituted or substituted with:
    (i) aryl,
    (ii) heteroaryl,
    (iii) —OH,
    (iv) —SH,
    (v) C₁₋₄ alkoxy,
    (vi) C₁₋₄ alkylthio,
    (vii) halo
    (viii) —NO₂
    (ix) —CO₂R¹¹, wherein R¹¹ is —H or C₁₋₄ alkyl,
    (x) —NH₂,
    (xi) —NH(C₁₋₄ alkyl)
    (xii) —N(C₁₋₄ alkyl)₂
    (xiii) —PO₃H₂,
    (xiv) —P(O)(OH) (OC₁₋₄ alkyl), or
    (xv) —P(O)(OR⁴)(R⁸) wherein R⁸ is
      (a) —H
      (b) C₁₋₅ alkyl,
      (c) aryl or
      (d) —CH₂-aryl,
(8) —NHSO₂R⁷,
(9) —SO₂NHCOR⁷,
(10) —CH₂SO₂NHCOR⁷,
(11) —CONHSO₂R⁷,
(12) —CH₂CONHSO₂R⁷,
(13) —NHSO₂NHCOR⁷,
(14) —NHCONHSO₂R⁷,
(15) —SO₂NHCONR⁴R⁷,
(16) —CH₂SO₂NHR⁷,
(17) —C(OH)(R⁸)—P(O) (OR⁶)₂,
(18) —P(O)(R⁸)(OR⁶),
(19) tetrazol-5-yl, substituted with R⁹ wherein R⁹ is
  (a) —H,
  (b) C₁₋₆ alkyl,
  (c) C₂₋₄ alkenyl,
  (d) C₁₋₄ alkoxy-C₁₋₄ alkyl
  (e) benzyl, either unsubstituted or substituted with
    (i) —NO₂,
    (ii) —NH₂,
    (iii) —OH, or
    (iv) —OCH₃,
(20) —CH₂-tetrazol-5-yl substituted with R⁹,
(21) —CONH-tetrazol-5-yl substituted with R⁹,
(22) -1,3,4-triazol-2-yl substituted with R¹⁰ wherein R¹⁰ is
  (a) —CN,
  (b) —NO₂,
  (c) —CF₃ or
  (d) —CO₂R⁴;
(23) 1,2,3-triazol-4-yl substituted with R¹⁰,
(24) —SO₂NHSO₂R⁷,
(25) —OH or

(26) —SO₂NHCON⟨ ⟩Z;

R² is:
(1) —H,
(2) —CO-aryl,
(3) C₃₋₇ cycloalkyl,
(4) halo,
(5) —OH,
(6) —OR⁷,
(7) polyfluoro-C₁₋₄ alkyl,
(8) —S(O)ₓR⁷,
(9) —COOR⁴,
(10) —SO₂H,
(11) —NR⁴R⁷,
(12) —NHCOR⁷,
(13) —NHCO₂R⁷
(14) —SO₂NR⁸R¹¹, wherein R¹¹ is
  (a) —H or
  (b) C₁₋₄ alkyl,
(15) —NO₂,
(16) —NHSO₂R⁷,
(17) —NHCONR⁴R⁷,
(18) —OCONR⁷R⁸,

(19) aryl,
(20) heteroaryl,
(21) —NHSO$_2$—polyfluorophenyl,
(22) —SO$_2$NH—heteroaryl,
(23) —SO$_2$NHCOR$^7$,
(24) —CONHSO$_2$R$^7$,
(25) —PO(OR$^4$)$_2$,
(26) —PO(OR$^4$)R$^8$,
(27) tetrazol-5-yl,
(28) —CONH(tetrazol-5-yl),
(29) —COR$_4$
(30) —SO$_2$NHCN,
(31) —CO-heteroaryl,
(32) —NHSO$_2$NR$^7$R$^8$, or
(33) C$_{1-6}$ alkyl, either unsubstituted or substituted with
  (a) —OH,
  (b) —guanidino,
  (c) —C$_{1-4}$ alkoxy,
  (d) —N(R$^4$)$_2$,
  (e) —CO$_2$R$^4$,
  (f) —CON(R$^4$)$_2$,
  (g) —O—COR$^4$
  (h) -aryl,
  (i) -heteroaryl,
  (j) —S(O)$_x$R$^7$
  (k) -tetrazol-5-yl,
  (l) —CONHSO$_2$R$^7$,
  (m) —SO$_2$NH—heteroaryl,
  (n) —SO$_2$NHCOR$^7$,
  (o) —PO(OR$^4$)$_2$,
  (p) —PO(OR$^4$)R$^9$,
  (q) —SO$_2$NHCN,
  (r) —NR$^{11}$COOR$^7$,
  (s) —morpholino,
  (t) —N(C$_{1-6}$ alkyl) piperazine or
  (u) —COR$^4$, with the proviso that the R$^2$ substituents can be the same or different; or if attached to the same carbon, two R$^2$ groups taken together represent:
    (a)=O,
    (b)=S or
    (c) —[(CH$_2$)$_{2-6}$]—;
R$^{2a}$, R$^{2b}$, R$^{3a}$ and R$^{3b}$ independently represent:
(1) C$_{1-5}$ alkyl,
(2) polyfluoro-C$_{1-5}$ alkyl,
(3) halo,
(4) hydroxy or
(5) C$_{1-5}$ alkoxy;
U, V and W are independently —CH= or —N= provided no more than one of U, V and W is —N= at one time;
Z is:
(1) —O—,
(2) —S(O)$_x$—,
(3) —N(R$^{12}$)—wherein R$^{12}$ is
  (a) —H or
  (b) —R$^{13}$ wherein R$^{13}$ is
    (i) C$_{1-4}$ alkyl,
    (ii) C$_{3-7}$ cycloalkyl
    (iii) aryl,
    (iv) heteroaryl,
    (v) polyfluoro-C$_{1-4}$ alkyl,
    (vi) polyfluoro-C$_{3-7}$ cycloalkyl or
    (vii) polyfluorophenyl;
(4) —N(COR$^{13}$)—,
(5) —N(CONHR$^{13}$)—,
(6) —N(CON(R$^{13}$)$_2$)—,
(7) —N(CO$_2$R$^{13}$)—,
(8) —N(SO$_2$NHR$^{13}$)—,
(9) —N(SO$_2$N(R$^{13}$)$_2$)—,
(10) —N(SO$_2$R$^{13}$)—, or
(11) —C(R$^2$)$_2$—,
X is:
(1) a single bond
(2) —SO$_2$—
(3) —O—
(4) —C(R$^2$)$_2$—
(5) —N(R$^{12}$)—
(6) —N(COR$^{13}$)—
(7) —N(CONHR$^{13}$)—
(8) —N(CON(R$^{13}$)$_2$)—
(9) —N(CO$_2$R$^{13}$)—
(10) —N(SO$_2$NHR$^{13}$)—
(11) —N(SO$_2$N(R$^{13}$)$_2$)—
(12) —N(SO$_2$R$^{13}$)—
Y is:
(1) —O—
(2) —S(O)$_x$— where x is 0, 1, or 2,
(3) —C(R$^2$)$_2$—
(4) —N(R$^{12}$)—
(5) —N(COR$^{13}$)—
(6) —N(CONHR$^{13}$)—
(7) —N(CON(R$^{13}$)$_2$)—
(8) —N(CO$_2$R$^{13}$)—
(9) —N(SO$_2$NHR$^{13}$)—
(10) —N(SO$_2$N(R$^{13}$)$_2$)—
(11) —N(SO$_2$R$^{13}$)—

The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The term "aryl" means phenyl or naphthyl either unsubstituted or substituted with one or two substituents which may be the same or different and are selected from the group consisting of halo, —NR$^4$, —CO$_2$R$^4$, C$_{1-4}$ alkyl, C$_{1-4}$ alkoxy, —NO$_2$, —CF$_3$, —OH and C$_{1-4}$ alkylthio.

The term "heteroaryl" means a 5- or 6-membered aromatic ring comprising 1 to 3 heteroatoms selected from O, N and S such as triazole, imidazole, thiazole, oxazole, isoxazole, oxadiazole, thiadiazole, pyridine, pyrazine, pyrimidine, or the like, either unsubstituted or substituted with 1 or 2 substituents selected from —OH, —SH, C$_{1-4}$ alkyl, C$_{1-4}$ alkoxy, —CF$_3$, halo, —NO$_2$, —CO$_2$R$^{11}$, or —N(R$^{11}$)$_2$ wherein the R$^{11}$ substituents are the same or different.

The term "halo" or "halogen", means —Cl, —Br, —I or —F.

One embodiment of the novel compounds of this invention is that wherein G is

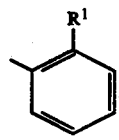

A class of compounds within this embodiment is that wherein:
E is (1) a single bond,
(2) —O— or
(3) —S—;

R is
(1) $C_{1-6}$ alkyl, either unsubstituted or substituted with
  (a) $C_{3-5}$ cycloalkyl,
  (b) —Cl,
  (c) —$CF_3$,
  (d) —$OCH_3$,
  (e) —$OC_2H_5$,
  (f) —$SCH_3$,
  (g) —$SC_2H_5$,
  (h) —F, or
  (i) phenyl;
(2) $C_{2-5}$ alkenyl,
(3) $C_{2-5}$ alkynyl, or
(4) $C_{3-5}$ cycloalkyl;

$R^1$ is
(1) —$CO_2H$,
(2) tetrazol-5-yl,
(3) —$NHSO_2R^7$,
(4) —$SO_2NH$-heteroaryl,
(5) —$CH_2SO_2NH$-heteroaryl,
(6) —$SO_2NHCOR^7$,
(7) —$CH_2SO_2NHCOR^7$,
(8) —$CONHSO_2R^7$,
(9) —$CH_2CONHSO_2R^7$,
(10) —$NHSO_2NHCOR^7$,
(11) —$NHCONHSO_2R^7$,
(12) —$SO_2NHCON(R^4)R^7$, or

(13) —SO2NHCONZ;

(14) —$SO_2NHSO_2R^7$ $R^2$ is:
(1) —H
(2) $C_{1-4}$ alkyl, either unsubstituted or substituted with:
  (a) —$CO_2R^4$,
  (b) —$OCOR^{4a}$,
  (c) —OH, or
  (d) aryl;
(3) $C_{2-4}$ alkenyl,
(4) —OH,
(5) —$NO_2$,
(6) —$NHCOR^7$,
(7) $C_{1-4}$ alkoxy,
(8) —$NHCO_2R^7$,
(9) —$NR^4R^7$ or
(10) —Cl, —F, or —Br; or two $R^2$ groups on the same carbon taken together represent =O or —$(CH_2)_{2-5}$—; and X is
(1) —$C(R^2)_2$— or
(2) a single bond;

Y is
(1) —$C(R^2)_2$— or
(2) —$N(R^{12})$—;

Z is
(1) —$N(R^{12})$—,
(2) —$C(R^2)_2$— or
(3) —O—;
(4) —$S(O)_x$— where x=0, 1, or 2.

Illustrative of this class of compounds are those shown in Table I and the Examples which follow:

TABLE I

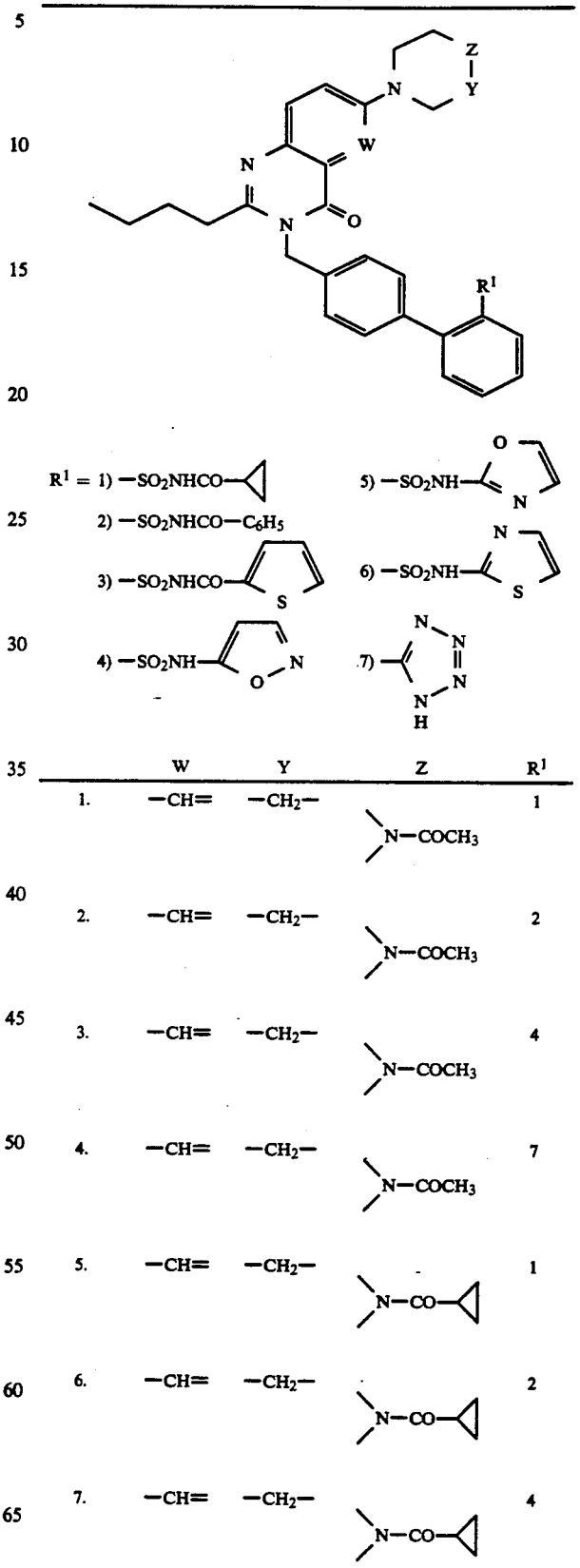

TABLE I-continued
| | | | | |
|---|---|---|---|---|
| 8. | —CH= | —CH₂— | 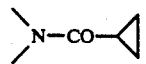 | 6 |
| 9. | —CH= | —CH₂— | 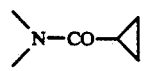 | 7 |
| 10. | —CH= | —CO— | 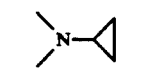 | 1 |
| 11. | —CH= | —CO— | 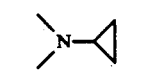 | 2 |
| 12. | —CH= | —CO— | 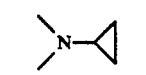 | 4 |
| 13. | —CH= | —CO— | 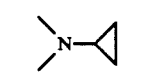 | 6 |
| 14. | —CH= | —CO— | 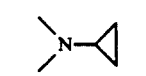 | 7 |
| 15. | —CH= | —CO— | 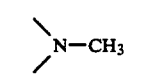 | 1 |
| 16. | —CH= | —CO— | 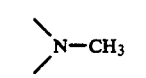 | 2 |
| 17. | —CH= | —CO— | 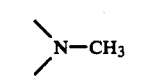 | 4 |
| 18. | —CH= | —CO— | 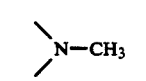 | 6 |
| 19. | —CH= | —CO— | 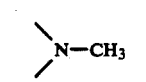 | 7 |
| 20. | —CH= | —CH₂— | —O— | 1 |
| 21. | —CH= | —CH₂— | —O— | 2 |
| 22. | —CH= | —CH₂— | —O— | 4 |
| 23. | —CH= | —CH₂— | —O— | 6 |
| 24. | —CH= | —CH₂— | —SO₂— | 1 |
| 25. | —CH= | —CH₂— | —SO₂— | 2 |
| 26. | —CH= | —CH₂— | —SO₂— | 4 |
| 27. | —CH= | —CH₂— | —SO₂— | 6 |
| 28. | —CH= | —CH₂— | —SO₂— | 7 |
| 29. | —CH= | —CH₂— |  | 1 |
| 30. | —CH= | —CH₂— |  | 2 |
| 31. | —CH= | —CH₂— |  | 4 |
| 32. | —CH= | —CH₂— |  | 6 |
| 33. | —CH= | —CH₂— | 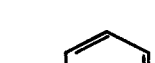 | 7 |
| 34. | —CH= | —CH₂— | 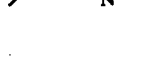 | 1 |
| 35. | —CH= | —CH₂— | 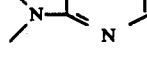 | 2 |
| 36. | —CH= | —CH₂— | 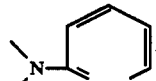 | 4 |
| 37. | —CH= | —CH₂— | 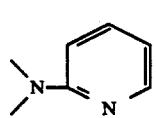 | 6 |
| 38. | —CH= | —CH₂— |  | 7 |
| 39. | —N= | —CH₂— | 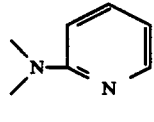 | 1 |
| 40. | —N= | —CH₂— | 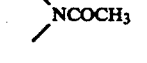 | 2 |
| 41. | —N= | —CH₂— | 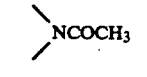 | 4 |
| 42. | —N= | —CH₂— | | 7 |

TABLE I-continued

| | | | | |
|---|---|---|---|---|
| 43. | —N= | —CH₂— | 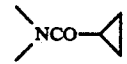 | 1 |
| 44. | —N= | —CH₂— | 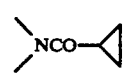 | 2 |
| 45. | —N= | —CH₂— | 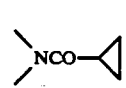 | 4 |
| 46. | —N= | —CH₂— |  | 6 |
| 47. | —N= | —CH₂— |  | 7 |
| 48. | —N= | —CO— |  | 1 |
| 49. | —N= | —CO— |  | 2 |
| 50. | —N= | —CO— | 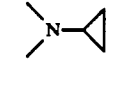 | 4 |
| 51. | —N= | —CO— | 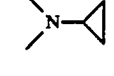 | 6 |
| 52. | —N= | —CO— | 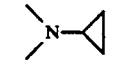 | 7 |
| 53. | —N= | —CO— | 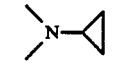 | 1 |
| 54. | —N= | —CO— | 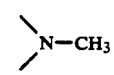 | 2 |
| 55. | —N= | —CO— | 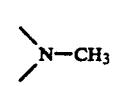 | 4 |
| 56. | —N= | —CO— | 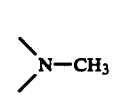 | 6 |
| 57. | —N= | —CO— |  | 7 |
| 58. | —N= | —CH₂— | —O— | 1 |
| 59. | —N= | —CH₂— | —O— | 2 |
| 60. | —N= | —CH₂— | —O— | 4 |
| 61. | —N= | —CH₂— | —O— | 6 |
| 62. | —N= | —CH₂— | —SO₂— | 1 |
| 63. | —N= | —CH₂— | —SO₂— | 2 |
| 64. | —N= | —CH₂— | —SO₂— | 4 |
| 65. | —N= | —CH₂— | —SO₂— | 6 |
| 66. | —N= | —CH₂— | —SO₂— | 7 |
| 67. | —N= | —CH₂— | 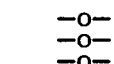 | 1 |
| 68. | —N= | —CH₂— | 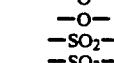 | 2 |
| 69. | —N= | —CH₂— | 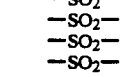 | 4 |
| 70. | —N= | —CH₂— |  | 6 |
| 71. | —N= | —CH₂— | 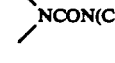 | 7 |
| 72. | —N= | —CH₂— | 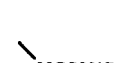 | 1 |
| 73. | —N= | —CH₂— | 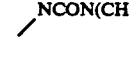 | 2 |
| 74. | —N= | —CH₂— | 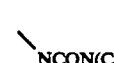 | 4 |
| 75. | —N= | —CH₂— | 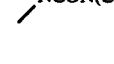 | 6 |
| 76. | —N= | —CH₂— |  | 7 |

Another embodiment of the novel compounds of this invention is that wherein G is R¹.

A class of compounds within this embodiment is that wherein:

E is (1) a single bond, (2) —O— or
(3) —S—;

R is
(1) $C_{1-6}$ alkyl, either unsubstituted or substituted with
  (a) $C_{3-5}$ cycloalkyl,
  (b) —Cl,
  (c) —CF$_3$,
  (d) —OCH$_3$,
  (e) —OC$_2$H$_5$,
  (f) —SCH$_3$,
  (g) —SC$_2$H$_5$,
  (h) —F, or
  (i) phenyl;
(2) $C_{2-5}$ alkenyl,
(3) $C_{2-5}$ alkynyl, or
(4) $C_{3-5}$ cycloalkyl;

$R^1$ is
(1) —CO$_2$H,
(2) tetrazol-5-yl,
(3) —NHSO$_2$R$^7$,
(4) —SO$_2$NH-heteroaryl,
(5) —CH$_2$SO$_2$NH-heteroaryl,
(6) —SO$_2$NHCOR$^7$,
(7) —CH$_2$SO$_2$NHCOR$^7$,
(8) —CONHSO$_2$R$^7$,
(9) —CH$_2$CONHSO$_2$R$^7$,
(10) —NHSO$_2$NHCOR$^7$,
(11) —NHCONHSO$_2$R$^7$,
(12) —SO$_2$NHCON(R$^4$)R$^7$ or

(13) —SO$_2$NHCON⟨ ⟩Z;

$R^2$ is:
(1) —H,
(2) $C_{1-4}$ alkyl, either unsubstituted or substituted with:
  (a) —CO$_2$R$^4$,
  (b) —OCOR$^{4a}$,
  (c) —OH, or
  (d) aryl;
(3) $C_{2-4}$ alkenyl,
(4) —OH,
(5) —NO$_2$,
(6) —NHCOR$^7$,
(7) $C_{1-4}$ alkoxy,
(8) —NHCO$_2$R$^7$,
(9) —NR$^4$R$^7$ or
(10) —Cl, —F, or —Br; or two R$^2$ groups on the same carbon taken together represent =O or —(CH$_2$)$_{2-5}$—;

Z is
(1) —N(R$^{12}$)—,
(2) —C(R$^2$)$_2$—, or
(3) —O—,

X is
(1) —C(R$^2$)$_2$— or
(2) a single bond; and

Y is
(1) —C(R$^2$)$_2$— or
(2) —N (R$^{12}$)—.

Illustrative of this class of compounds are those shown in Table II and the Examples which follow:

TABLE II

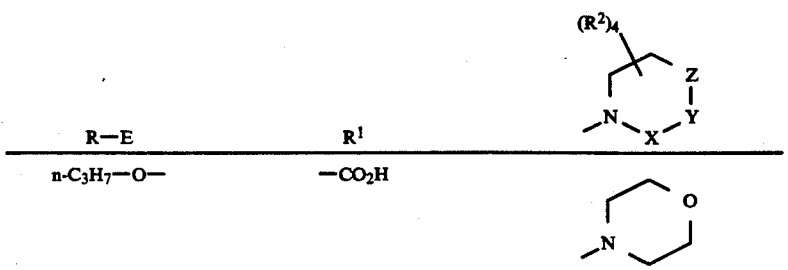

| R—E | R$^1$ | 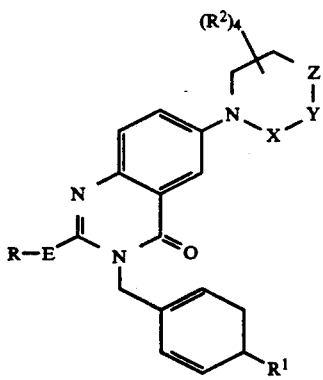 |
|---|---|---|
| n-C$_3$H$_7$—O— | —CO$_2$H |  |

TABLE II-continued

| | | |
|---|---|---|
| ▷−CH₂− | tetrazole (5-yl, NH) | N-methylmorpholin-3-one (attached at CH₂) |
| CH₂=CH−CH₂− | −NHSO₂CH₃ | N-methylthiomorpholine (attached at CH₂) |
| cyclopentyl | −CH₂SO₂NHCO−▷ | 4-methyl-1-(cyclopropanecarbonyl)piperazin-2-one (attached at CH₂) |
| CF₃CH₂CH₂− | −CONHSO₂C₂H₅ | 1-methylpiperazine (attached at CH₂, NH free) |
| n-C₃H₇−S− | −SO₂NHCON(C₂H₅)₂ | 4-methyl-1-(N-methylcarbamoyl)-2,3-dioxopiperazine (attached at CH₂) |
| C₆H₅−CH₂− | −SO₂NHCON(morpholino) | 4-methylpiperazin-2-one (attached at CH₂, NH free) |
| n-C₄H₉− | −CH₂CONHSO₂CH₃ | 4-methylmorpholin-3-one (attached at CH₂) |
| F(CH₂)₃− | −NHSO₂NHCO−▷ | 4-methyl-1-(cyclopropanecarbonyl)piperazine (attached at CH₂) |
| n-C₃H₇− | −NHCONHSO₂CH₃ | 1-methyl-4-(N,N-dimethylcarbamoyl)-2,5-dioxopiperazine (attached at CH₂) |
| n-C₃H₇ | −NHCONHSO₂CH₃ | 1-methylpiperidine (attached at CH₂) |
| n-C₃H₇ | −NHCONHSO₂CH₃ | 5,5-dimethyl-1,3-dimethylbarbituric acid (attached at C-5) |

TABLE II-continued

| n-C$_3$H$_7$ | —NHCONHSO$_2$CH$_3$ |  |
|---|---|---|

The compounds of this invention are prepared in accordance with the following Reaction Schemes:

SCHEME I
Piperazine And Morpholine Syntheses

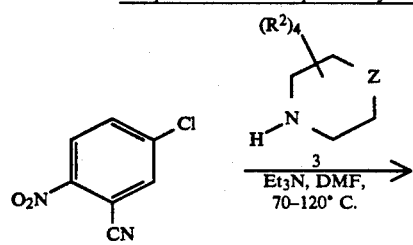
2

$\xrightarrow{\underset{\text{Et}_3\text{N, DMF,}}{3}}$
70–120° C.

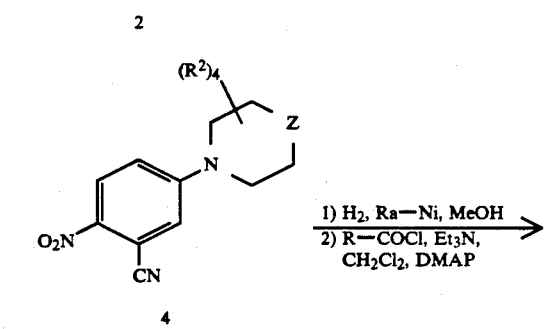
4

1) H$_2$, Ra—Ni, MeOH
2) R—COCl, Et$_3$N, CH$_2$Cl$_2$, DMAP

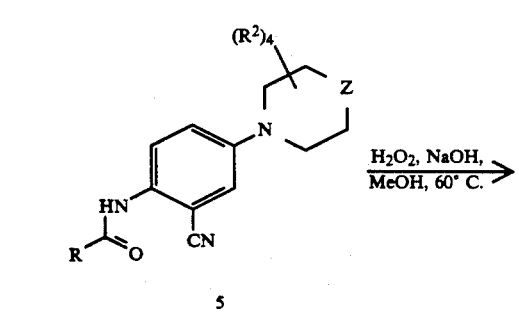
5

$\xrightarrow{\underset{\text{MeOH, 60° C.}}{\text{H}_2\text{O}_2\text{, NaOH,}}}$

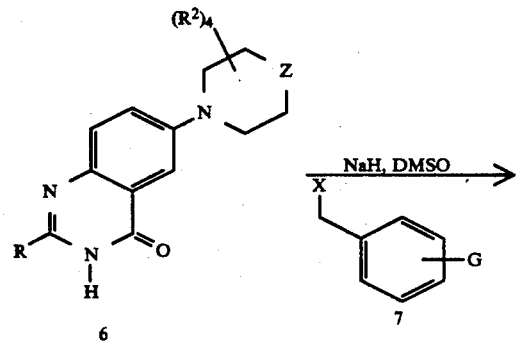
6

$\xrightarrow{\text{NaH, DMSO}}$

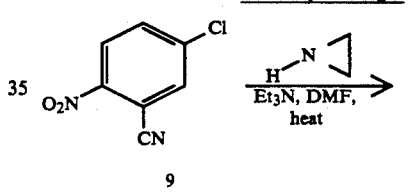
7

-continued
SCHEME I
Piperazine And Morpholine Syntheses

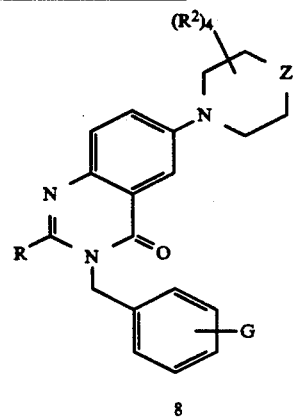
8

SCHEME 2
Carbonyl Analogs

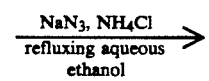
9

$\xrightarrow[\text{heat}]{\text{Et}_3\text{N, DMF,}}$

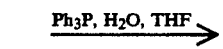
10

$\xrightarrow[\text{ethanol}]{\underset{\text{refluxing aqueous}}{\text{NaN}_3\text{, NH}_4\text{Cl}}}$

11

$\xrightarrow{\text{Ph}_3\text{P, H}_2\text{O, THF}}$

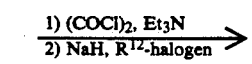
12

1) (COCl)$_2$, Et$_3$N
2) NaH, R$^{12}$-halogen

-continued
SCHEME 2
Carbonyl Analogs

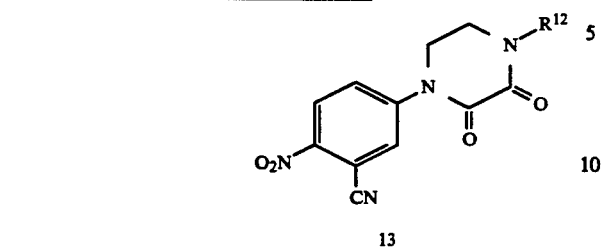

13

The steps used in Scheme I from the nitrobenzonitrile 4 to the final product 8 are the same as for 13 to final product.

SCHEME 3
Carbonyl Analogs

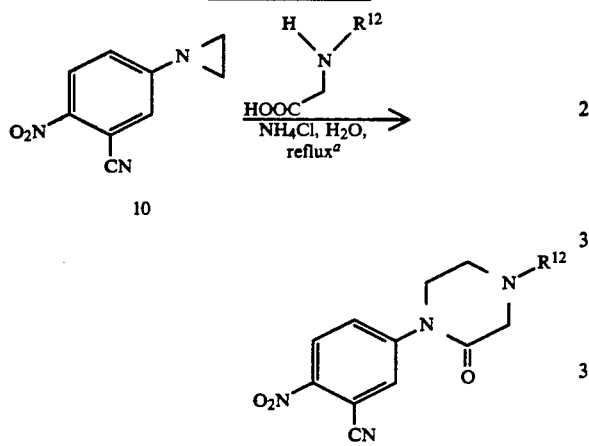

15

*See D.C. Rees, J. Het. Chem. (1987), 24, 1297-1300.

The steps used in Scheme 1 from the nitrobenzonitrile 4 to the final product 8 are the same as for 15 to final product.

SCHEME 4: Carbonyl Analogs

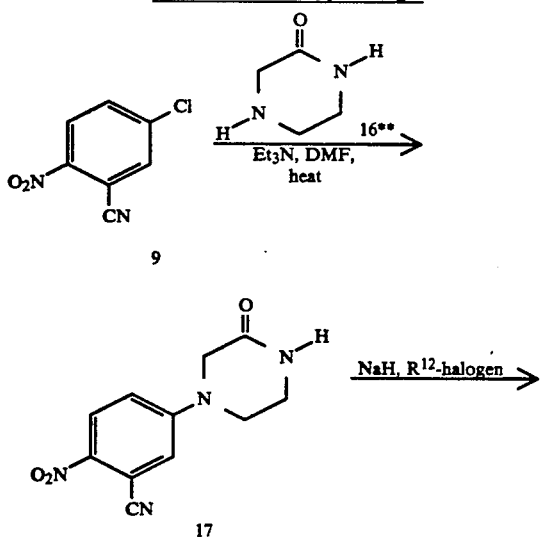

17

-continued
SCHEME 4: Carbonyl Analogs

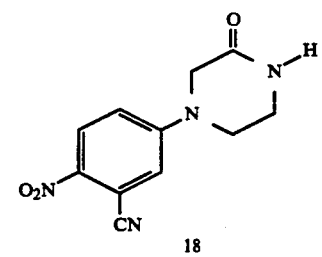

18

**See S.R. Aspinall, J. Am. Chem. Soc., (1940), 62, 1202.

The steps used in Scheme 1 from the nitrobenzonitrile 4 to the final product 8 are the same as for 18 to final product.

SCHEME 5: Urea Derivatives

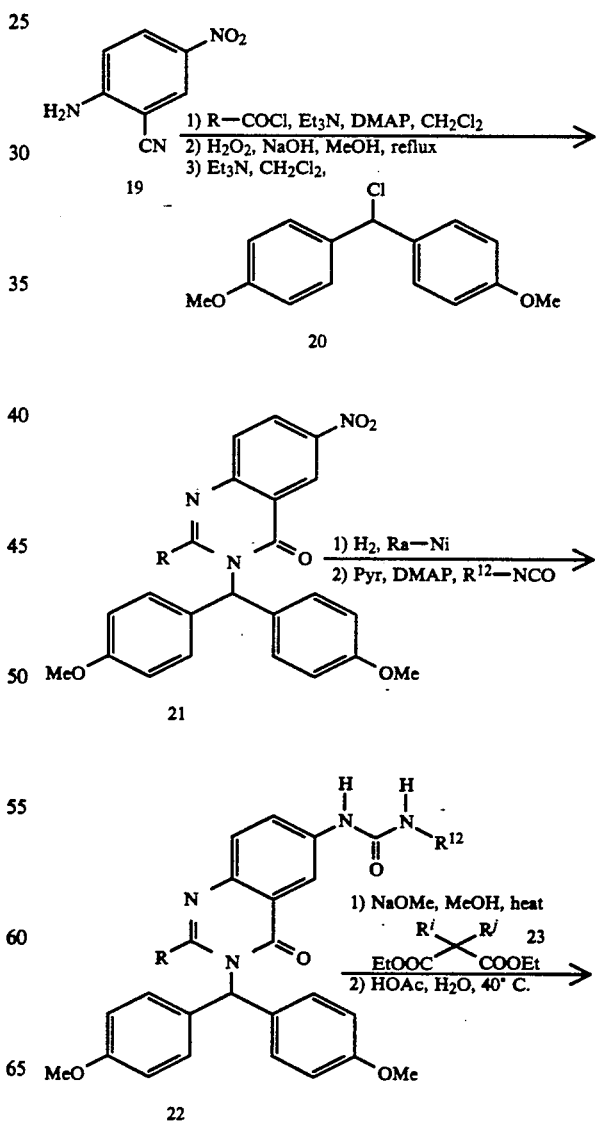

-continued
SCHEME 5: Urea Derivatives

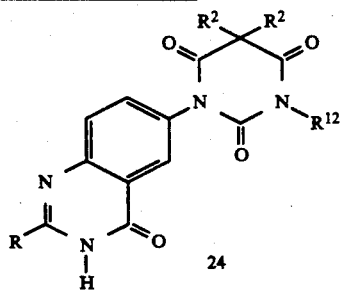

Quinazolinone 24 may carried on to the final product using the same methods used for 6 in Scheme 1.

SCHEME 6: Pyridopyrimidine Analogs

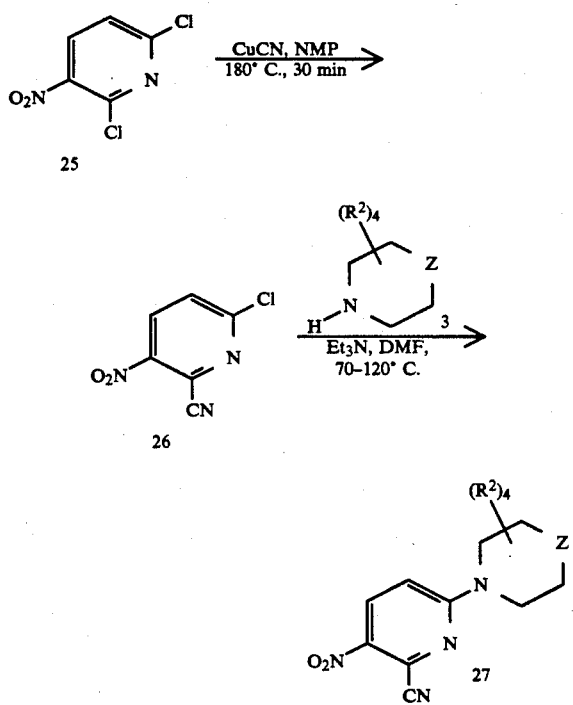

Commercially available 25 may be converted to the nitrile derivative 26 (see N. L. Colbry, E. F. Elslager, L. M. Werbel, *J. Heterocyclic Chem.*, (1984), 21, 1521–1525) then to the aminated derivative 27 as shown in Scheme 6. The pyridine 27 may then be converted to the corresponding pyridopyrimidine following the procedures as used for intermediate 4 as shown in Scheme 1.

| Abbreviations | |
|---|---|
| DMF | Dimethyl formamide |
| Me | Methyl |
| Et | Ethyl |
| t-BOC | t-Butoxycarbonyl |
| DMSO | Dimethyl sulfoxide |
| DMAP | 4-dimethylaminopyridine |
| EtOAc | Ethyl acetate |
| Et$_2$O | Diethyl ether |
| AcOH | Acetic acid |
| TFA | Trifluoracetic acid |
| NMP | N-methyl-2-pyrrolidinone |

The novel process of this invention comprises the condensation of compounds VI and VII to yield VIII. To one skilled in the art it will be apparent that if Z in a final product is —NH— or a nitrogen with a functional group substituent, that nitrogen will require protection during this step followed by deprotection if desired. Similarly if R$^1$

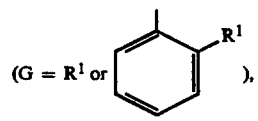

has a terminal nitrogen such as in —SO$^2$NH$_2$, it also will require appropriate protection followed by deprotection and derivatization if desired.

The condensation is conducted in a polar aprotic solvent such as DMF, or DMSO, in the presence of a strong base such as: an alkali metal hydride preferably sodium hydride; an alkali metal alkane or aromatic such as n-butyl lithium, or phenyl lithium or the like. The reaction temperature is not critical and may be conducted at about 0° C. to about 100° C., but preferably and most conveniently at about room temperature or about 20°–30° C. The time required for the reaction to go to completion will depend on the temperature, and will vary from about 4 hours to about 24 hours. It is convenient to let it proceed for about 16 hours (overnight) at about room temperature.

t-Butyl or t-BOC protective groups are readily removed by treating the protected compound with anisole in TFA overnight at about room temperature.

The deprotected nitrogens can readily be acylated by treatment with the appropriate acyl chloride in the presence of a catalyst such as DMAP and an acid acceptor such as Et$_3$N or pyridine in a solvent such as pyridine, CH$_2$Cl$_2$ or the like.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, H$_2$SO$_4$, H$_3$PO$_4$, methanesulfonic, toluenesulfonic, maleic, fumaric, camphorsulfonic. The non-toxic, physiologically acceptable salts are preferred, although other salts are also useful, e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freezedrying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml), homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin, and the suspension was used for 100 assay tubes. Samples tested for screening were done in duplicate. To the membrane preparation (0.25 ml) there was added $^{125}I$-$Sar^1Ile^8$-angiotensin II [obtained from New England Nuclear] (10 μl; 20,000 cpm) with or without the test sample, and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist, which gives 50% displacement of the total specifically bound $^{125}I$-$Sar^1Ile^8$-angiotensin II, was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethanesulfonyl fluoride (PMSF)(0.1 mM)]. (For screening of compounds generally duplicates of tubes are used). To the membrane preparation (0.5 ml) there was added $^3H$-angiotensin II (50 mM) (10 μl), with or without the test sample, and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist, which gives 50% displacement of the total specifically bound $^3H$-angiotensin II, was presented as a measure of the efficacy of such compounds as AII antagonists.

Using the methodology described above, representative compounds of the invention were evaluated and were found to exhibit an activity of atleast $IC_{50} < 50$ μM, thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure and angina. These compounds may also be expected to be useful in the treatment of primary and secondary hyperaldosteronism; renal diseases such a diabetic nephropathy, glomerulonephritis, glomerular sclerosis, nephrotic syndrome, hypertensive nephrosclerosis, end stage, renal disease, used in renal transplant therapy, and to treat renovascular hypertension, sclerderma, left ventricular dysfunction, systolic and diasystolic dysfunction, diabetic retinopathy and in the management of vascular disorders such as migraine, Raynaud's disease, and as prophylaxis to minimize the atherosclerotic process and neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, -adrenergic antagonists such as timolol maleate, adrenergic agonists such as epinephrine and carbonic anhydrase inhibitors such as MK-507.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient, depending upon the nature and severity of disease, the patient's weight, special diets then being followed by a patient, concurrent medication and other factors, which those skilled in the art will recognize, the dosage range will generally be about 1 to 1000 mg. per patient per day which can be administered in single or multiple doses. Perferably, the dosage range will be about 5 to 500 mg. per patient per day; more preferably about 5 to 300 mg. per patient per day.

The compounds of this invention can also be administered in combination with other antihypertensives and-/or diuretics. For example, the compounds of this invention can be givein in combination with diuretics such as hydrochlorothiazide, chlorothiazide, chlorothalidone, methyclothiazide, furosemide, ethacrynic acid, triamterene, amiloride, atriopeptin and spironolactone; calcium channel blocker, such as diltiazem, felodipine, nifedipine, amlodipine, nimodipine, isradipine, nitrendipine and verapamil; $\beta$-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; $\alpha$-adrenergic antagonists such as prazosin, doxazosin, and terazosin; sympatholytic agents such as methyldopa, (alone or with ANP) clonidine and guanabenz, atriopeptidase inhibitors (alone or with ANP) such as UK-79300; serotonin antagonists such as ketanserin; $A_2$-adenosine receptor agonists such as CGS 22492C; potassium channel agonists such as pinacidil and cromakalim; and various other antihypertensive drugs including reserpine, minoxidil, guanethidine, hydralazine hydrochloride and sodium nitroprusside as well as combination of the above-named drugs as well as admixtures and combinations thereof.

Combinations useful in the management of congestive heart failure include, in addition, compounds of this invention with cardiac stimulants such as dobutamine and xamoterol and phosphodiesterase inhibitors including amrinone and mirinone.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 5-500 milligrams per day range can be effectively combined at levels at the 1.0-500 milligrams per day range with the following compounds at the indicated per day dose range: hydrochlorothiazide (6-100 mg) chlorothiazide (125-500 mg), ethacrynic acid (5-200 mg), amiloride (5-20 mg), furosemide (5-80 mg), propanolol (10-480 mg), timolol maleate (1-20 mg.), methyldopa (125-2000 mg), felodipine (1-20 mg), nifedipine (5-120 mg), nitrendipine (5-60 mg) and diltizaem (30-540 mg). In addition, triple drug combinations of hydrochlorothiazide (5-100 mg) plus amiloride (5-20 mg) plus angiotensin II antagonist of this invention (1-500 mg) or hydrochlorothiazide (5-100 mg) plus timolol maleate (5-60) plus an angiotensin II antagonist of this invention (1-500 mg) or hydrochlorothiazide (5-200 mg) and nifedipine (5-60 mg) plus an angiotensin II antagonist of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elizir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotype and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and buspirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of formula (I) and their incorporation into pharmaceutical compositions and as such are not to be considered as limiting the invention set forth in the claims appended hereto. All reactions as appropriate were carried out under an atmosphere of dry nitrogen under standard conditions for those skilled in the art.

EXAMPLE 1

2-n-Butyl-6-(morpholin-4-yl)-3-[(2'-(N-cyclopropanecarbonylsulfonamido)biphenyl-4-yl)methyl]-quinazolin-4(3H)-one

Step A

Preparation of methyl 5-chloro-2-nitrobenzoate

To a solution of 10 g (49.6 mmol) of 5-chloro-2-nitrobenzoic acid and 9 mL (64.5 mmol) Et$_3$N in 300 ml CH$_2$Cl$_2$ at 0° C. was added 4.6 mL (59.5 mmol) methyl chloroformate. The cold bath was removed and after 10 minutes, 0.200 mL methanol was added. Bubbles of CO$_2$ could be seen rising from the solution. After 2 hours, the mixture was diluted with Et₂O, was washed with 5% HCl, was washed with saturated NaHCO₃ solution, was washed with brine, was dried over MgSO₄ and decolorized with charcoal, then was stripped of solvent in vacuo to give the product. $R_f$ 0.35 in 15% EtOAc/hexane, visualized by UV; ¹H-NMR (400 MHz, CDCl₃): δ 7.92 (d, J=8.6 Hz, 1H), 7.69 (d, J=2.3 Hz, 1H), 7.59 (dd, J₁=2.2 Hz, J₂=8.8 Hz, 1H), 3.94 (s, 3H).

Step B

Preparation of methyl 5-(morpholin-4-yl)-2-nitrobenzoate

A solution of 2.0 g (9.28 mmol) product from Step A and 1.6 mL (18.6 mmol) morpholine in 20 mL DMF was heated to 90° C. for 6 hours. After the mixture had cooled to room temperature, the DMF was stripped off in vacuo. The crude material was then redissolved in methanol and stirred with 20 g Amberlyst-A26® for about 20 minutes. The mixture was then stripped of solvent and used without further purification in the next step. $R_f$ 0.20 in 40% EtOAc/hexane, visualized by UV and visible light.

Step C

Preparation of methyl 2-amino-5-(morpholin-4-yl) benzoate

The nitro compound from Step B above was dissolved in 75 mL THF and 25 mL MeOH. This solution was added to about 2 g methanol-washed Raney® nickel (Aldrich, equivalent to W-2). The atmosphere above the solution was replaced with hydrogen and allowed to stir overnight. After replacing the hydrogen atmosphere with nitrogen, the mixture was diluted with CH₂Cl₂, and was filtered (CAUTION: Raney® nickel is pyrophoric and must be kept wet, preferably with CH₂Cl₂, to prevent ignition. A blanket of nitrogen is also recommended. The catalyst was destroyed by adding water and concentrated HCl). The filtrate was stripped of solvent in vacuo, and was chromatographed on silica gel under medium pressure using 35% EtOAc/hexane to give 1.36 g of the product in, 62% yield over 2 steps. $R_f$ 0.21 in 40% EtOAc/hexane, visualized by UV and ninhydrin stain (black).

Step D

Preparation of methyl 5-(morpholin-4-yl)-2-pentanoylamino-benzoate

To a solution of 1.36 g (5.74 mmol) of product from Step C, 1.6 mL Et₃N, and about 15 mg DMAP in 20 mL DMF was added 0.886 mL (7.47 mmol) valeryl chloride. After 20 minutes the mixture was poured into NaHCO₃ solution and extracted 3 times with ether. The combined organic material was dried over Na₂SO₄, stripped of solvent in vacuo, and was chromatographed on silica gel under medium pressure using 30% EtOAc/hexane to give the product. $R_f$ 0.29 in 40% EtOAc/hexane, visualized by UV and ammonium molybdate/ceric sulfate stain; ¹H-NMR (400 MHz, CDCl₃): δ 10.75 (br s, 1H), 8.62 (d, J=9.2 Hz, 1H), 7.50 (d, J=2.9 Hz, 1H), 3.94 (dd, J1=3.0 Hz, J2=9.2 Hz, 1H), 3.90 (s, 3H), 3.85 (3 line m, 4H), 3.10 (3 line m, 4H), 2.39 (3 line m, 2H), 1.71 (5 line m, 2H), 1.39 (6 line m, 2H), 0.93 (3 line m, 3H).

Step E

Preparation of 2-n-butyl-6-(morpholin-4-yl) quinazolin-4(3H)-one

The ester obtained from Step D was heated to 65° C. for 10 minutes with 2 mL 50% NaOH in 50 mL methanol. The mixture was cooled to room temperature then about 1 mg phenolphthalein was added. The mixture was acidified with concentrated HCl until colorless. The mixture was diluted with brine and extracted 3 times with CH₂Cl₂. The combined organic material was washed with brine, dried over Na₂SO₄, stripped of solvent in vacuo to give 1.57 g of the free acid corresponding to the ester product of Step D, 89% yield over 2 steps. $R_f$ 0.18 in 1/60/39 HOAc/EtOAc/hexane, visualized by UV and ammonium molybdate/ceric sulfate stain (blue).

The acid (1.57 g, 5.11 mmol) was dissolved in 80 mL DMF to which was added 2.1 mL (15.3 mmol) Et₃N, about 50 mg DMAP, and 0.728 mL (6.13 mmol) valeryl chloride. After 10 minutes the mixture was heated to 110° C. After 1 hour, 3.8 g (30.7 mmol) ammonium carbonate was added over about 8 minutes (CAUTION: Frothing occurs and could cause boilover). After 30 minutes the mixture was cooled to room temperature and poured into water. The precipitate was collected on filtration through a medium fritted funnel. The solid was redissolved in methanol to which was added 2 mL 50% NaOH. The mixture was heated to reflux for 30 minutes to complete the conversion of the bis-amide to quinazolinone. The mixture was cooled to room temperature, phenolphthalein was added and the mixture was acidified with concentrated HCl until colorless. Water was added and the precipitated solid was collected. The mother liquor was heated again and a second crop of crystals was taken to give a combined total of 958 mg of product in 65% yield. $R_f$ 0.25 in 40% EtOAc/hexane, visualized by UV and ammonium molybdate/ceric sulfate stain; ¹H-NMR (400 MHz, DMSO-d₆): δ 11.99 (br s, 1H), 7.50 (m, 2H), 7.38 (m, 1H), 3.76 (3 line m, 4H), 3.18 (3 line m, 4H), 2.55 (3 line m, 2H), 1.68 (5 line m, 2H), 1.33 (6 line m, 2H), 0.90 (3 line m, 3H).

Step F

Preparation of 2-n-butyl-6-(morpholin-4-yl)-3-[(2'-(N-t-butylsulfonamido)biphenyl-4-yl)methyl] quinazolin-4(3H)-one To a solution of 200 mg (0.696 mmol) of product from Step E in 10 mL DMF was added 31 mg (0.766 mmol) 60% NaH in oil followed by 319 mg (0.835 mmol) [(2'-N-t-butylsulfonamido)biphenyl-4-yl]methyl bromide. The mixture was allowed to stir overnight. The mixture was diluted with brine and extracted three times with Et₂O. The combined organic material was washed with brine, dried over Na₂SO₄, stripped of solvent in vacuo, was chromatographed on silica gel under medium pressure using 1/40/59 AcOH/EtOAc/hexane, and was stripped in vacuo from toluene to give 262 mg of product in, 64% yield. $R_f$ 0.11 in 1/40/59 AcOH/EtOAc/hexane, visualized by UV (fluorescent blue under longwave UV; O-alkylated material fluoresces yellow under long-wave UV and runs slightly higher on TLC); ¹H-NMR (400 MHz, CDCl₃): δ 8.16 (4 line m, 1H), 7.67–7.40 (mm, 8H), 7.27 (m, 2H), 5.46 (br, s, 2H), 3.90 (3 line m, 4H), 3.49 (s, 1H), 3.28 (3 line m, 4H), 2.74 (3 line m, 2H), 1.79 (5 line m, 2H), 1.43 (6 line m, 2H), 0.97 (s, 9H), 0.95 (3 line m, 3H).

Step G

Preparation of 2-n-butyl-6-(morpholin-4-yl)-3-[(2'-sulfonamidobiphenyl-4-yl)methyl]quinazolin-4(3H)-one A solution of 262 mg (0.444 mmol) of product from Step F and 0.048 mL (0.444 mmol) anisole in TFA was stirred overnight. The TFA was removed in vacuo and the crude material was redissolved in $CH_2Cl_2$ and washed with saturated $NaHCO_3$ solution. Solvent was again removed in vacuo and the material was recrystallized from hexane/$CHCl_3$ to give 169 mg of the title compound 109, 71% yield. $R_f$ 0.21 in 60% EtOAc/hexane, visualized by UV (fluorescent blue under longwave UV; $^1$H-NMR (400 MHz, $CDCl_3$): δ 8.16 (4 line m, 1H), 7.66–7.56 (mm, 3H), 7.54–7.40 (mm, 4H), 7.29 (m, 3H), 5.47 (br s, 2H), 4.14 (s, 2H), 3.90 (3 line m, 4H), 3.28 (3 line m, 4H), 2.77 (3 line m, 2H), 1.78 (5 line m, 2H), 1.43 (6 line m, 2H), 0.94 (3 line m, 3H).

Step H

Preparation of 2-n-butyl-6-(morpholin-4-yl)-3-[(2'-(N-cyclopropanecarbonylsulfonamido)biphenyl-4-yl)methyl]-quinazolin-4(3H)-one To a solution of 60 mg (0.113 mmol) of product from Step G and about 5 mg DMAP in 6 mL pyridine was added 0.082 mL (0.901 mmol) cyclopropanecarbonyl chloride. After 2 hours 0.100 mL methanol was added and the solution was stripped of pyridine in vacuo. The crude material was redissolved in $CH_2Cl_2$ and washed with water. The organic layer was extracted 3 times with 2% aqueous KOH. The combined aqueous material was reacidified with AcOH and extracted three times with $CH_2Cl_2$. The combined organic material was dried over $Na_2SO_4$, stripped of solvent in vacuo, was chromatographed on silica gel under medium pressure using 1/10/89 $NH_4OH$/MeOH/$CH_2Cl_2$ then again in 1/60/39 AcOH/EtOAc/hexane, and was stripped in vacuo from toluene to give 39 mg of the title compound, 57% yield. $R_f$ 0.15 in 1/10/89 $NH_4OH$/MeOH/$CH_2Cl_2$, visualized by UV; $^1$H-NMR (300 MHz, $CDCl_3$): δ 8.25 (4 line m, 1H), 7.66–7.50 (mm, 4H), 7.46–7.14 (mm, 6H), 5.46 (s, 2H), 3.89 (3 line m, 4H), 3.26 (3 line m, 4H), 2.81 (3 line m, 2H), 1.81 (5 line m, 2H), 1.45 (6 line m, 2H), 1.06 (m, 1H), 0.95 (3 line m, 3H), 0.86 (m, 2H), 0.66 (m, 2H); MS (FAB) m/e 601 (M+1).

EXAMPLE 2

2-n-Butyl-6-(4-cyclopropanecarbonylpiperazin-1-yl)-3-[(2'-(N-cyclopropanecarbonylsulfonamido)biphenyl-4-yl)methyl]quinazolin-4(3H)-one.

Step A

Preparation of 2-n-butyl-6-(4-t-butoxycarbonyl piperazin-1-yl)quinazolin-4(3H)-one A solution of 4.0 g (21.9 mmol) 5-chloro-2-nitrobenzonitrile, 4.90 g (26.3 mmol) t-butoxycarbonylpeperazine, and 6.1 ml (43.8 mmol) $Et_3N$ in 20 mL DMF was heated to 70° C. for 6 hours. Solvent was removed in vacuo, the crude product was partitioned between saturated $NaHCO_3$ solution, brine, and $CH_2Cl_2$. The organic layer was removed and the aqueous layer was extracted twice more with $CH_2Cl_2$. The combined organic material was dried over $Na_2SO_4$, stripped of solvent in vacuo to give 2-cyano-4-(4-t-butoxycarbonylpiperazin-1-yl) nitrobenzene. The material was sufficiently pure to use without further purification. $R_f$ 0.26 in 40% EtOAc/hexane, bright yellow under normal white light.

The nitro compound from above was hydrogenated using the same procedure as in Example 1, Step C. The crude product 2-cyano-4-(4-t-butoxycarbonylpiperazin-1-yl) aniline, was acylated using the same procedure as Example 1, Step D. The crude product was chromatographed on silica gel under medium pressure using 45% EtOAc/hexane to give the corresponding amide. $R_f$ 0.19 in 40% EtOAc/hexane, visualized by UV and ammonium molybdate/ceric sulfate stain.

The amide was dissolved in 100 mL methanol. To the solution was added 26 mL (65.7 mmol) 2.5N NaOH and 15 mL 30% $H_2O_2$. The solution was heated to 60° C. for about three hours. Upon cooling to room temperature, the mixture was acidified with concentrated HCl to the colorless point of phenolphthalein. Brine was added and the mixture was extracted 3 times with $CH_2Cl_2$. The combined organic material was dried over $Na_2SO_4$, stripped of solvent in vacuo, and was recrystallized from EtOAc to give 1.87 g 2-n-butyl-6-(4-t-butoxycarbonylpiperazin-1-yl)quinazolin-4(3H)-one, 22% yield over 4 steps. $R_f$ 0.19 in 60% EtOAc/hexane, visualized by UV (fluorescent light blue under long-wave UV); $^1$H-NMR (400 MHz, $CDCl_3$): δ9.88 (br s, 1H), 7.61 (m, 2H), 7.42 (dd, $J_1$=2.9 Hz, $J_2$=9.1 Hz, 1H), 3.61 (3 line m, 4H), 3.25 (3 line m, 4H), 2.71 (3 line m, 2H), 1.81 (5 line m, 2H), 1.49 (s, 9H), 1.47 (6 line m, 2H), 0.98 (3 line m, 3H).

Step B

Preparation of 2-n-butyl-6-(4-t-butoxycarbonylpiperazin-1-yl)-3-[(2'-(N-t-butylsulfonamido) biphenyl-4-yl)methyl]quinazolin-4(3H)-one This compound was obtained using a procedure similar to that of Example 1, Step F. Using 303 mg (0.785 mmol) 2-n-butyl-6-(4-t-butoxycarbonylpiperazine-1-yl) quinazolin-4(3H)-one, 300 mg (0.785 mmol) [(2'-N-t-butylsulfonamido)biphenyl-4-yl]methyl bromide, 31 mg (0.863 mmol) 60% NaH in oil, in 10 mL DMF, 281 mg of product was isolated after chromatography on silica gel under medium pressure using 40% EtOA/hexane, 52% yield. $R_f$ 0.10 in 40% EtOAc/hexane, visualized by UV (fluorescent blue under long-wave UV; O-alkylated material is fluorescest yellow under long-wave UV and runs slightly higher on TLC); $^1$H-NMR (400 MHz, $CDCl_3$): δ 8.16 (d, J=8.0 Hz, 1H), 7.67-7.41 (mm, 7H), 7.27 (m, 3H), 5.46 (br s, 2H), 3.61 (3 line m, 4H), 3.49 (s, 1H), 3.26 (3 line m, 4H), 2.74 (3 line m, 2H), 1.78 (5 line m, 2H), 1.49 (s, 9H), 1.43 (6 line m, 2H), 0.97 (s, 9H), 0.94 (3 line m, 3H).

Step C

Preparation of 2-n-butyl-6-piperazin-1-yl)-3-[(2'-sulfonamidobyphenyl-4-yl)methyl]quinazolin-4(3H)-one This compound was obtained using a procedure similar to that used in Example 1 Step G. Using 276 mg (0.401 mmol) product from Step B and 0.087 mL (0.802 mmol) anisole, in 10 mL TFA, 105 mg product was isolated after stripping off the TFA in vacuo, treating with saturated $NaHCO_3$ and extracting with $CH_2Cl_2$, drying over Na₂SO₄, and recrystallizing from hexane/MeOH/CHCl₃, 49% yield. R$_f$ 0.25 in 1/10/89 NH₄OH/MeOH/CH₂Cl₂, visualized by UV.

Step D

Preparation of 2-n-butyl-6-(4-cyclopropanecarbonylpiperazin-1-yl)-3-[(2'-N-cyclopropanecarbonylsulfonamidobiphenyl-4-yl)methyl]quinazolin-4(3H)-one This compound was obtained using a procedure similar to that used in Example 1 Step H. Using 105 mg (0.197 mmol) product of Step C, about 5 mg DMAP, 0.179 mL (1.97 mmol) cyclopropanecarbonyl chloride, in 10 mL pyridine, 127 mg of product was isolated after addition of 0.100 mL MeOH, stripping of solvents in vacuo, addition of water and extraction with CH₂Cl₂, drying over Na₂SO₄, stripping from toluene in vacuo, and chromatography on silica gel under medium pressure using 1/75/24 AcOH/EtOAc/hexane, and again stripping from toluene in vacuo, 96% yield. R$_f$ 0.22 in 1/75/24 AcOH/EtOAc/hexane, visualized by UV (fluorescent blue under long-wave UV) and ammonium molybdate/ceric sulfate stain; ¹H-NMR (400 MHz, CDCl₃): δ 8.25 (4 line m, 1H), 7.62 (m, 2H), 7.59–7.51 (m, 2H), 7.44 (4 line m, 1H), 7.36–7.20 (4 line m, 4H), 7.28 (4 line m, 1H), 5.44 (br s, 2H), 3.86 (br m, 4H), 3.31 (br m, 4H), 2.81 (3 line m, 2H), 1.81 (mm, 3H), 1.44 (6 line m, 2H), 1.10 (m, 1H), 1.03 (m, 2H), 0.95 (3 line m, 3H), 0.86 (m, 2H), 0.82 (m, 2H), 0.66 (m, 2H); MS (FAB) m/e 668 (M+1).

Employing procedures substantially as described in Example 2 with appropriate starting materials the compounds described in Table III were prepared.

TABLE III

| Ex. | R—E | G | Z | Mass Spec (FAB) m/e |
|---|---|---|---|---|
| 3. | n-C₃H₇— | 2-(SO₂NHCO-cyclopropyl)phenyl | 2-(dimethylamino)pyridin-N-yl | 663 (M + 1) |
| 4. | n-C₃H₇— | 2-(SO₂NHCO-cyclopropyl)phenyl | N-CO-cyclopropyl | 654 (M + 1) |
| 5. | n-C₃H₇— | SO₂NHCO-cyclopropyl | 2-(dimethylamino)pyridin-N-yl | 587 (M + 1) |
| 6. | n-C₄H₉— | 2-(1H-tetrazol-5-yl)phenyl | N—CO—CH₃ | 563 (M + 1) |

EXAMPLE 7

Typical Pharmaceutical Compositions Containing a Compound of the Invention as Active Ingredient A: Dry Filled Capsules Containing 50 mg of Active Ingredient Per Capsule

| Ingredient | Amount per capsule (mg) |
| --- | --- |
| Active Ingredient | 50 |
| Lactose | 149 |
| Magnesium stearate | 1 |
| Capsule (size No. 1) | 200 |

The active ingredient can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the active ingredient (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of the active ingredient (50 mg) pregelatinized starch USP (82 mg), microcrystalline cellulose (82 mg) and magnesium stearate (1 mg).

D: Suppository

Typical suppository formulations for rectal administration can contain the active ingredient (1-25 mg), butylated hydroxyanisole (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypersive and/or a diuretic and/or an angiotension converting enzyme and/or a calcium channel blocker in pharmaceutically effective amounts as described, for example, in C above.

E: Injection

A typical injectible formulation would contain the active ingredient (5.42 mg), sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotension converting enzyme inhibitor and/or a calcium channel blocker.

What is claimed is:

1. A compound of structural formula:

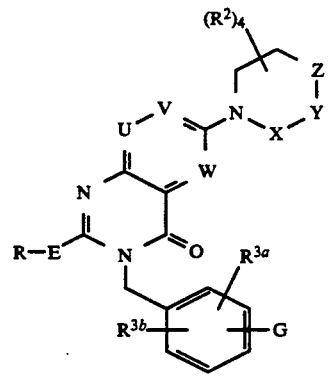

or a pharmaceutically acceptable salt thereof, wherein:

G is
(1) $R^1$ or

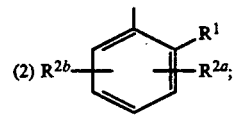

E is
(1) a single bond,
(2) —CH(OH)—,
(3) —O—,
(4) —CO—,
(5) —S(O)$_x$(CH$_2$)$_s$— wherein x is 0, 1, or 2, and s is 0-5, or
(6) —NR$^3$(CH$_2$)$_s$— wherein R$^3$ is
  (a) —H,
  (b) C$_{2-4}$ alkanoyl,
  (c) C$_{1-6}$ alkyl,
  (d) C$_{2-6}$ alkenyl,
  (e) C$_{3-7}$ cycloalkyl,
  (f) phenyl, or
  (g) benzyl;

R is
(1) aryl,
(2) heteroaryl,
(3) C$_{3-7}$ cycloalkyl,
(4) polyfluoro-C$_{1-4}$ alkyl,
(5) —H,
(6) C$_{2-6}$ alkenyl,
(7) C$_{2-6}$ alkynyl,
(8) C$_{1-6}$ alkyl, either unsubstituted or substituted with:
  (a) aryl,
  (b) C$_{3-7}$ cycloalkyl,
  (c) halo,
  (d) —NH$_2$,
  (e) —NH(C$_{1-4}$ alkyl),
  (f) —N(C$_{1-4}$ alkyl)$_2$,
  (g) —OR$^4$, wherein R$^4$ is
    (i) —H,
    (ii) aryl,
    (iii) heteroaryl,
    (iv) C$_{1-6}$ alkyl, or
    (v) aryl-C$_{1-6}$ alkyl;
  (h) —COOR$^4$,
  (i) —NHSO$_2$R$^4$, or
  (j) —SO$_2$NHR$^5$, wherein R$^5$ is
    (i) —H (ii) $C_{1-5}$ alkyl,
(iii) aryl or
(iv) —$CH_2$—aryl;

$R^1$ is
(1) —$CO_2R^4$
(2) —$SO_3R^6$, wherein $R^6$ is
  (a) —H
  (b) —$CH(R^4)$—O—CO—$R^{4a}$ wherein $R^{4a}$ is
    (i) $C_{1-6}$ alkyl,
    (ii) aryl or
    (iii) —$CH_2$—aryl;
(3) —$P(O)(OR^6)_2$,
(4) —$CONHNHSO_2CF_3$,
(5) —$SO_2NHCN$,
(6) —$P(O)(OR^6)(OR^4)$,
(7) —$SO_2NHR^7$, wherein $R^7$ is
  (a) —H
  (b) aryl,
  (c) heteroaryl,
  (d) $C_{3-7}$ cycloalkyl,
  (e) polyfluoro-$C_{1-4}$ alkyl, or
  (f) $C_{1-10}$ alkyl, either unsubstituted or substituted with:
    (i) aryl,
    (ii) heteroaryl,
    (iii) —OH,
    (iv) —SH,
    (v) $C_{1-4}$ alkoxy,
    (vi) $C_{1-4}$ alkylthio
    (vii) halo
    (viii) —$NO_2$
    (ix) —$CO_2R^{11}$, wherein $R^{11}$ is —H or $C_{1-4}$ alkyl,
    (x) —$NH_2$,
    (xi) —$NH(C_{1-4}$ alkyl)
    (xii) —$N(C_{1-4}$ alkyl$)_2$
    (xiii) —$PO_3H_2$,
    (xiv) —$P(O)(OH)(OC_{1-4}$ alkyl), or
    (xv) —$P(O)(OR^4)(R^8)$ wherein $R^8$ is
      (a) —H
      (b) —$C_{1-5}$ alkyl,
      (c) -aryl or
      (d) —$CH_2$—aryl,
(8) —$NHSO_2R^7$,
(9) —$SO_2NHCOR^7$,
(10) —$CH_2SO_2NHCOR^7$,
(11) —$CONHSO_2R^7$,
(12) —$CH_2CONHSO_2R^7$,
(13) —$NHSO_2NHCOR^7$,
(14) —$NHCONHSO_2R^7$,
(15) —$SO_2NHCONR^4R^7$,
(16) —$CH_2SO_2NHR^7$,
(17) —$C(OH)(R^8)$—$P(O)(OR^6)_2$,
(18) —$P(O)(R^8)(OR^6)$,
(19) tetrazol-5-yl, substituted with $R^9$ wherein $R^9$ is
  (a) —H,
  (b) $C_{1-6}$ alkyl,
  (c) $C_{2-4}$ alkenyl,
  (d) $C_{1-4}$ alkoxy-$C_{1-4}$ alkyl
  (e) benzyl, either unsubstituted or substituted with
    (i) —$NO_2$,
    (ii) —$NH_2$,
    (iii) —OH, or
    (iv) —$OCH_3$,
(20) —$CH_2$-tetrazol-5-yl substituted with $R^9$,
(21) —$CONH$-tetrazol-5-yl substituted with $R^9$,
(22) —1,3,4-triazol-2-yl substituted with $R^{10}$ wherein $R^{10}$ is
  (a) —CN,
  (b) —$NO_2$,
  (c) —$CF_3$ or
  (d) —$CO_2R^4$;
(23) 1,2,3-triazol-4-yl substituted with $R^{10}$,
(24) —$SO_2NHSO_2R^7$,
(25) —OH or

(26) —$SO_2NHCON$Z;

$R^2$ is:
(1) —H,
(2) —CO-aryl,
(3) $C_{3-7}$ cycloalkyl,
(4) halo,
(5) —OH,
(6) —$OR^7$,
(7) polyfluoro-$C_{1-4}$ alkyl,
(8) —$S(O)_xR^7$,
(9) —$COOR^4$,
(10) —$SO_2H$,
(11) —$NR^4R^7$,
(12) —$NHCOR^7$,
(13) —$NHCO_2R^7$,
(14) —$SO_2NR^8R^{11}$, wherein $R^{11}$ is
  (a) —H or
  (b) $C_{1-4}$ alkyl,
(15) —$NO_2$
(16) —$NHSO_2R^7$,
(17) —$NHCONR^4R^7$,
(18) —$OCONR^7R^8$,
(19) aryl,
(20) heteroaryl,
(21) —$NHSO_2$polyfluorophenyl,
(22) —$SO_2NH$—heteroaryl,
(23) —$SO_2NHCOR^7$,
(24) —$CONHSO_2R^7$,
(25) —$PO(OR^4)_2$,
(26) —$PO(OR^4)R^8$,
(27) tetrazol-5-yl,
(28) —$CONH$(tetrazol-5-yl),
(29) —$COR^4$
(30) —$SO_2NHCN$,
(31) —CO—heteroaryl,
(32) —$NHSO_2NR^7R^8$, or
(33) $C_{1-6}$ alkyl, either unsubstituted or substituted with
  (a) —OH,
  (b) —guanidino,
  (c) —$C_{1-4}$ alkoxy,
  (d) —$N(R^4)_2$,
  (e) —$CO_2R^4$,
  (f) —$CON(R^4)_2$,
  (g) —O—$COR^4$
  (h) -aryl,
  (i) -heteroaryl,
  (j) —$S(O)_xR^7$
  (k) -tetrazol-5-yl,
  (l) —$CONHSO_2R^7$,
  (m) —$SO_2NH$—heteroaryl,
  (n) —$SO_2NHCOR^7$,
  (o) —$PO(OR^4)_2$,
  (p) —$PO(OR4)R^9$,
  (q) —$SO_2NHCN$,
  (r) —$NR^{11}COOR^7$, (s) -morpholino,
(t) —N($C_{1-6}$ alkyl)piperazine or
(u) —$COR^4$, with the proviso that the $R^2$ groups can be the same or different; or two $R^2$ groups joined to the same carbon taken together represent
  (a) =O
  (b) =S or
  (c) —[$(CH_2)_{2-6}$]—;
$R^{2a}$, $R^{2b}$, $R^{3a}$ and $R^{3b}$ independently represent
  (1) $C_{1-5}$ alkyl,
  (2) polyfluoro-$C_{1-5}$ alkyl,
  (3) halo;
  (4) hydroxy or
  (5) $C_{1-5}$ alkoxy;
U, V and W are —CH= or
Z is:
  (1) —O—,
  (2) —S(O)$_x$—
  (3) —N($R^{12}$)— wherein $R^{12}$ is
    (a) —H or
    (b) —$R^{13}$ wherein $R^{13}$ is
      (i) $C_{1-4}$ alkyl,
      (ii) $C_{3-7}$ cycloalkyl
      (iii) aryl,
      (iv) heteroaryl,
      (v) polyfluoro-$C_{1-4}$ alkyl,
      (vi) polyfluoro-$C_{3-7}$ cycloalkyl, or
      (vii) polyfluorophenyl;
  (4) —N(COR$^{13}$)—,
  (5) —N(CONHR$^{13}$)—,
  (6) —N(CON(R$^{13}$)$_2$)—,
  (7) —N(CO$_2$R$^{13}$)—,
  (8) —N(SO$_2$NHR$^{13}$)—,
  (9) —N(SO$_2$N(R$^{13}$)$_2$)—,
  (10) —N(SO$_2$R$^{13}$)—, or
  (11) —C(R$^2$)$_2$—,
X is
  (1) a single bond
  (2) —SO$_2$—
  (3) —O—
  (4) —C(R$^2$)$_2$—
  (5) —N(R$^{12}$)—
  (6) —N(COR$^{13}$)—
  (7) —N(CONHR$^{13}$)—
  (8) —N(CON(R$^{13}$)$_2$)—
  (9) —N(CO$_2$R$^{13}$)—
  (10) —N(SO$_2$NHR$^{13}$)—
  (11) —N(SO$_2$N(R$^{13}$)$_2$)—
  (12) —N(SO$_2$R$^{13}$)—
Y is
  (1) —O—
  (2) —S(O)$_x$— where x is 0, 1, or 2,
  (3) —C(R$^2$)$_2$—
  (4) —N(R$^{12}$)—
  (5) —N(COR$^{13}$)—
  (6) —N(CONHR$^{13}$)—
  (7) —N(CON(R$^{13}$)$_2$)—
  (8) —N(CO$_2$R$^{13}$)—
  (9) —N(SO$_2$NHR$^{13}$)—
  (10) —N(SO$_2$N(R$^{13}$)$_2$)—
  (11) —N(SO$_2$R$^{13}$)—.
2. The compound of claim 1 wherein G is

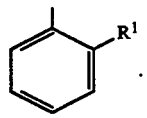

3. The compound of claim 2 wherein:
E is
  (1) a single bond,
  (2) —O— or
  (3) —S—;
R is
  (1) $C_{1-6}$ alkyl, either unsubstituted or substituted with:
    (a) $C_{3-5}$ cycloalkyl,
    (b) —Cl,
    (c) —CF$_3$,
    (d) —OCH$_3$,
    (e) —OC$_2$H$_5$,
    (f) —SCH$_3$,
    (g) —SC$_2$H$_5$,
    (h) —F, or
    (i) phenyl;
  (2) $C_{2-5}$ alkenyl,
  (3) $C_{2-5}$ alkynyl, or
  (4) $C_{3-5}$ cycloalkyl;
$R^1$ is
  (1) —CO$_2$H,
  (2) tetrazol-5-yl,
  (3) —NHSO$_2$R$^7$,
  (4) —SO$_2$NH—heteroaryl,
  (5) —CH$_2$SO$_2$NH-heteroaryl,
  (6) —SO$_2$NHCOR$^7$,
  (7) —CH$_2$SO$_2$NHCOR$^7$,
  (8) —CONHSO$_2$R$^7$,
  (9) —CH$_2$CONHSO$_2$R$^7$
  (10) —$_2$NHSO$_2$NHCOR$^7$ or
  (11) —NHCONHSO$_2$R$^7$
  (12) —SO$_2$NHCON(R$^4$)R$^7$
  (13) —SO$_2$NHCON Z
$R^2$ is:
  (1) H,
  (2) $C_{1-4}$ alkyl, either unsubstituted or substituted with:
    (a) —CO$_2$R$^4$,
    (b) —OCOR$^{4a}$,
    (c) —OH, or
    (d) —aryl;
  (3) $C_{2-4}$ alkenyl,
  (4) —OH,
  (5) -NO$_2$,
  (6) -NHCOR$^7$,
  (7) —$C_{1-4}$ alkoxy,
  (8) —NHCO$_2$R$^7$,
  (9) —NR$^4$R$^7$ or
  (10) —Cl, —F, or —Br; or two R$^2$ groups on the same carbon taken together represent =O or —(CH$_2$)$_{2-5}$—; and
X is
  (1) —C(R$^2$)$_2$— or
  (2) a single bond;
Y is
  (1) —C(R$^2$)$_2$— or
  (2) —N(R$^{12}$)$_2$—;
Z is
  (1) —N(R$^{12}$)—,
  (2) —N(COR$^{13}$)—, (3) —N(CONHR$^{13}$)—, or
(4) —N(CON(R$^{13}$)$_2$)—,
(5) —O—
(6) —S—.

4. The compound of claim 3 of structural formula:

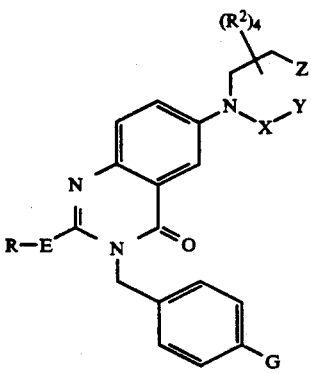

or a pharmaceutically acceptable salt thereof selected from the group of compounds consisting of those in the following table:

| R—E | R$^1$ | Z |
|---|---|---|
| n-C$_4$H$_9$— | ![](SO₂NH—CO—cyclopropyl, o-tolyl) | —O— |
| n-C$_4$H$_9$— | ![](SO₂NH—CO—cyclopropyl, o-tolyl) | (CH₃)₂N—CO—cyclopropyl |
| n-C$_3$H$_7$— | ![](SO₂NH—CO—cyclopropyl, o-tolyl) | 6-(dimethylamino)pyridin-2-yl |
| n-C$_3$H$_7$— | | (CH₃)₂N—CO—cyclopropyl |
| n-C$_3$H$_7$— | —SO₂NH—CO—cyclopropyl | 6-(dimethylamino)pyridin-2-yl |
| n-C$_4$H$_9$— | 5-(o-tolyl)tetrazole | (CH₃)₂N—COCH₃ |

5. The compound of claim 1 wherein G is R$^1$.
6. The compound of claim 5 wherein:
E is
  (1) a single bond,
  (2) —O— or
  (3) —S—;
R is
  (1) C$_{1-6}$ alkyl, either unsubstituted or substituted with:
    (a) C$_{3-5}$ cycloalkyl,
    (b) —Cl,
    (c) —CF$_3$,
    (d) —OCH$_3$,
    (e) —OC$_2$H$_5$,
    (f) —SCH$_3$,
    (g) —SC$_2$H$_5$
    (h) —F, or
    (i) phenyl;
  (2) C$_{2-5}$ alkenyl,
  (3) C$_{2-5}$ alkynyl, or
  (4) C$_{3-5}$ cycloalkyl;
R$^1$ is
  (1) —CO$_2$H,
  (2) tetrazol-5-yl,
  (3) —NHSO$_2$R$^7$,
  (4) —SO$_2$NH-heteroaryl,
  (5) —CH$_2$SO$_2$NH-heteroaryl,
  (6) —SO$_2$NHCOR$^7$,
  (7) —CH$_2$SO$_2$NHCOR$^7$,
  (8) —CONHSO$_2$R$^7$,
  (9) —CH$_2$CONHSO$_2$R$^7$,
  (10) —$_2$NHSO$_2$NHCOR$^7$ or
  (11) —NHCONHSO$_2$R$^7$
  (12) —SO$_2$NHCON(R$^4$)R$^7$
  (13) —SO$_2$NHCON Z
R$^2$ is:
  (1) H,
  (2) C$_{1-4}$ alkyl, either unsubstituted or substituted with:
    (a) —CO$_2$R$^4$,
    (b) —OCOR$^{4a}$,
    (c) —OH, or
    (d) -aryl;
  (3) C$_{2-4}$ alkenyl,
  (4) —OH,
  (5) —NO$_2$,
  (6) —NHCOR$^7$,
  (7) —C$_{1-4}$ alkoxy,
  (8) —NHCO$_2$R$^7$,
  (9) —NR$^4$R$^7$ or
  (10) —Cl, —F, or —Br; or two R$^2$ groups on the same carbon taken together represent =O; and
X is
  (1) —C(R$^2$)$_2$— or
  (2) a single bond;
Y is
  (1) —C(R$^2$)$_2$— or
  (2) —N(R$^{12}$)$_2$—;
Z is
  (1) —N(R$^{12}$)—,
  (2) —N(COR$^{13}$)—,
  (3) —N(CONHR$^{13}$)—, or
  (4) —N(CON(R$^{13}$)$_2$)—,
  (5) —O—
  (6) —S—.
7. The compound of claim 6 wherein E-R is

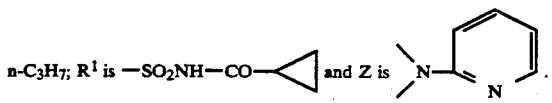

8. A pharmaceutical composition comprising a pharmaceutically acceptable carrier and a therapeutically effective amount of a compound of claim 1.

9. The composition of claim 8 which includes another antihypertensive selected from a diuretic selected from hydrochlorothiazide, chlorothiazide, chlorthalidone, methyclothiazide, furosemide, ethacrynic acid, triamterene, amiloride, atriopeptin and spironolactone; a calcium channel blocker, selected from diltiazem, felodipine, nifedipine, amlodipine, rumodipine, isradapine, nitrendipine and verapamil; a β-adrenergic antagonist selected from timolol, atenolol, metoprolol, propanolol, nadolol and pindolol; an angiotensin converting enzyme inhibitor selected from enalapril, lisinopril, captopril, ramipril, quinapril and zofenopril; a renin inhibitor selected from A-69729, FK-906 and FK-744; an α-adrenergic antagonist selected from prazosin, doxazosin, and terazosin; a sympatholytic agent selected from methyl- dopa, clonidine and guanabenz; the atriopeptadase inhibitor UK-79300 (alone or with ANP); the serotonin antagonist, ketanserin; the $A_2$-adenosine receptor agonist CGS 22492C; a potassium channel agonist selected from pinacidil and cromakalim; another antihypertensive drug selected from reserpine, minoxidil, guanethidine, hydralazine, hydrochloride and sodium nitroprusside; a cardiac stimulant selected from dobutamine and xamoterol; a phosphodiesterase inhibitor selected from amrinone and milrinone or combinations of the above-named drugs.

10. A method of treating hypertension which comprises administering to a patient in need of such treatment a pharmaceutically effective amount of a compound of claim 1.

11. An ophthalmological formulation for the treatment of ocular hypertension comprising an ophthalmologically acceptable carrier and an effective ocular antihypertensive amount of a compound of claim 1.

12. A method of treating ocular hypertension comprising administering to a patient in need of such treatment an effective ocular antihypertensive amount of a compound of claim 1.

* * * * *